US007825143B2

(12) United States Patent
Toenjes et al.

(10) Patent No.: US 7,825,143 B2
(45) Date of Patent: Nov. 2, 2010

(54) METHOD FOR CONTROLLING THE YEAST-TO-FILAMENTOUS GROWTH TRANSITION IN FUNGI

(75) Inventors: Kurt A. Toenjes, Billings, MT (US); David K. Butler, Billings, MT (US)

(73) Assignee: Montana State University - Billings, Billings, MT (US)

( * ) Notice: Subject to any disclaimer, the term of this patent is extended or adjusted under 35 U.S.C. 154(b) by 640 days.

(21) Appl. No.: 11/775,852

(22) Filed: Jul. 10, 2007

(65) Prior Publication Data

US 2009/0018173 A1 Jan. 15, 2009

(51) Int. Cl.
*A61K 31/425* (2006.01)
(52) U.S. Cl. .................................. 514/369
(58) Field of Classification Search ........... 514/369
See application file for complete search history.

(56) References Cited

U.S. PATENT DOCUMENTS

| | | | |
|---|---|---|---|
| 5,834,309 A | 11/1998 | Thompson et al. |
| 5,955,593 A | 9/1999 | Korsmeyer |
| 5,981,721 A | 11/1999 | Mohan |
| 6,225,335 B1 | 5/2001 | Tang et al. |
| 6,562,796 B2 | 5/2003 | Baldwin et al. |
| 6,613,889 B2 | 9/2003 | Borders et al. |
| 6,706,766 B2 | 3/2004 | Yuan et al. |
| 7,144,905 B2 | 12/2006 | Yuan et al. |
| 2003/0060663 A1 | 3/2003 | Griffin et al. |
| 2004/0266846 A1 | 12/2004 | Yuan et al. |
| 2006/0037091 A1 | 2/2006 | Gurtner et al. |

OTHER PUBLICATIONS

Nucci, M. and K.A. Marr, Emerging fungal diseases. Clin Infect Dis, 2005. 41(4): p. 521-6.
Pfaller, M.A. and D.J. Diekema, Epidemiology of invasive candidiasis: a persistent public health problem. Clin Microbiol Rev, 2007. 20(1): p. 133-63.
Diezmann, S., et al., Phylogeny and evolution of medical species of Candida and related taxa: a multigenic analysis. J Clin Microbiol, 2004. 42(12): p. 5624-35.
Butler, G., et al., Evolution of pathogenicity and sexual reproduction in eight *Candida* genomes. Nature, 2009. 459(7247): p. 657-62.
Fitzpatrick, D.A., et al., A fungal phylogeny based on 42 complete genomes derived from supertree and combined gene analysis. BMC Evol Biol, 2006. 6: p. 1-16.
D. Butler, O. All, J. Goffena, T. Loveless, T. Wilson, & K. Toenjes, The GRR1 gene of *Candida albicans* is involved in the negative control of pseudohyphal morphogenesis, Fungal Genetics and Biology, 2006, pp. 573-582, vol. 43, Elsevier, Amsterdam, The Netherlands.

(Continued)

*Primary Examiner*—Shengjun Wang
(74) *Attorney, Agent, or Firm*—Antoinette M. Tease

(57) ABSTRACT

A method for controlling yeast-to-filamentous growth transition in fungi comprising contacting a fungal cell with an anti-fungal small molecule in an amount effective to reduce or inhibit the yeast-to-filamentous growth transition, wherein the anti-fungal small molecule is 5-(p-Bromobenzylidine)-α-isopropyl-4-oxo-2-thioxo-3-thiozolidineacetic acid or an analog thereof. A method for treating fungal infections comprising contacting one or more fungal cells with an anti-fungal small molecule in an amount effective to control the fungal infection, wherein the anti-fungal small molecule is 5-(p-Bromobenzylidine)-α-isopropyl-4-oxo-2-thioxo-3-thiozolidineactic acid or an analog thereof.

2 Claims, 4 Drawing Sheets

OTHER PUBLICATIONS

N. Fedorova, J. Badger, G. Robson, J. Wortman, & W. Nierman, Comparative analysis of programmed cell death pathways in filamentous fungi, BMC Genomics, 2005, pp. 1-14, vol. 6, Fedorova, London, United Kingdom.

D. Warnock, Trends in the Epidemiology of Invasive Fungal Infections, Japan Journal of Medical Mycology, 2006, pp. 1-12, vol. 48, Shun Kosha Inc., Tokoyo, Japan.

F. Madeo, E. Herker, C. Maldener, S. Wissing, S. Lachelt, M. Herlan, M. Feher, K. Lauber, S. Sigrist, S. Wesselborg, & K. Frohlich, A Caspase-Related Protease Regulates Apoptosis in Yeast, Molecular Cell, 2002, pp. 911-917, vol. 9, Cell Press, Cambridge, MA USA.

S. Saville, A. Lazell, C. Monteagudo, & J. Lopez-Ribot, Engineered Control of Cell Morphology in Vivo Reveals Distinct Roles for Yeast and Filamentous Form of *Candida albicans* during infection, Eukaryotic Cell, 2003, pp. 1053-1060, vol. 0.4, American Society for Microbiology, Washington, DC USA.

H. Lo, J. Kohler, B. DiDomenico, D. Loebenberg, A. Cacciapuoti, & G. Fink, Nonfilamentous *C. albicans* Mutants are Avrulent, Cell, 1997, pp. 939-949, vol. 90, Cell Press, Cambridge, MA USA.

R. S. Care, J. Trevethick, K. M. binley, & P. E. Sudbery, The MET3 promoter: a new tool for *Candida albicans* molecular genetics, Molecular Microbiology, 1999, pp. 792-798, vol. 34/4, Blackwell Science Ltd., Malden, MA USA.

M. Edmond, S. Wallace, D. McClish, M. Pfaller, R. Jones, & R. Wenzel, Nosocomial Bloodstream Infections in the United States Hospitals: A three-year Analysis, Clinical Infectious Diseases, 1999, pp. 239-244, vol. 29, Infectious Disease Society of America, Arlington, VA USA.

METHOD FOR CONTROLLING THE YEAST-TO-FILAMENTOUS GROWTH TRANSITION IN FUNGI

BACKGROUND OF THE INVENTION

1. Field of the Invention

The present invention relates generally to the field of molecular biology, and more specifically, to a method for controlling the yeast-to-filamentous growth transition in fungi.

2. Description of the Related Art

The present invention addresses the need to treat and/or control human fungal infections, such as those caused by *Candida albicans* (*C. albicans*). *C. albicans* causes both superficial and disseminated (systemic) infections in humans, and is the leading cause of fungal disease in humans [1]. *C. albicans* is an opportunistic pathogen of immunocompromised hosts, including AIDS patients, individuals undergoing cancer chemotherapy, individuals receiving immunosuppressive drugs in preparation for tissue transplants, individuals receiving antibiotic treatments and individuals with central venous catheters. Studies indicate that up to 90% of AIDS patients suffer from oropharyngeal and esophageal candidiasis, in which *C. albicans* is the major causative agent [2]. It is estimated that *C. albicans* infections result in approximately 5,000 deaths per year in the United States [3]. The high incidence of fungal disease in the immunocompromised patient population indicates a need for better anti-fungal treatment modalities and anti-fungal drugs.

*C. albicans* is able to grow in different morphological forms, such as budding yeast (round or oval cells) and a range of filamentous forms that include true hyphae and pseudohyphae [4]. An essential component of the virulence of *C. albicans* is its ability to change between the yeast growth form and the filamentous growth forms. As used herein, the term "filamentous growth forms" includes both hyphal growth forms and pseudohyphal growth forms. Mutations that block transitions between these growth forms, and therefore restrict the organism to one of these two growth forms, also significantly reduce the virulence of the organism in mouse models of disseminated candidiasis [5, 11]. Thus, one way of controlling fungal infections in humans may be to prevent or inhibit the yeast-to-filamentous growth transition through small bioactive molecules.

The present invention is based on the unexpected discovery that the small molecule 5-(p-Bromobenzylidine)-α-isopropyl-4-oxo-2-thioxo-3-thiozolidineacetic acid (hereafter referred to as BH3I-1), a previously identified inducer of programmed cell death (PGD) in mammalian cells, inhibits the yeast-to-filamentous growth transition in *C. albicans*. In mammalian cells, POD is regulated by the Bcl-2 family proteins Bcl-2, Bcl-1x, Bak and Bax. The Bak/Bax proteins induce PGD by permeabilizing the outer mitochondrial membrane, causing the release of death-promoting factors such as cytochrome C and activation of the caspase cascade. Bcl-2 and Bcl-1x are anti-PGD proteins in that they directly antagonize Bak/Bax through protein-protein interactions. The small molecule BH3I-1 induces PGD by specifically binding to Bcl-1x, thereby preventing the antagonistic interaction between Bcl-1x and the Bak/Bax proteins. Surprisingly, especially in light of our discovery of the novel anti-fungal properties of BH3I-1, bioinformatics approaches have indicated that fungal genomes do not encode recognizable Bcl-2 family proteins or proteins with Bcl-2-homology-3 domains [6, 7]. This suggests that BH3I-1 is acting on a target in *C. albicans* that does not contain a BH3 domain and that is unrelated to the known target of BH3I-1 in mammalian cells.

BRIEF SUMMARY OF THE INVENTION

The present invention is a method for controlling yeast-to-filamentous growth transition in fungi comprising contacting a fungal cell with an anti-fungal small molecule in an amount effective to reduce or inhibit the yeast-to-filamentous growth transition, wherein the anti-fungal small molecule is 5-(p-Bromobenzylidine)-α-isopropyl-4-oxo-2-thioxo-3-thiozolidineacetic acid.

In an alternate embodiment, the present invention is a method for controlling the yeast-to-filamentous growth transition in fungi comprising contacting a fungal cell with an anti-fungal small molecule in an amount effective to reduce or inhibit the yeast-to-filamentous growth transition, wherein the anti-fungal small molecule is an analog of 5-(p-Bromobenzylidine)-α-isopropyl-4-oxo-2-thioxo-3-thiozolidineacetic acid.

In yet another alternate embodiment, the present invention is a method for controlling the yeast-to-filamentous growth transition in fungi comprising contacting a fungal cell with an anti-fungal small molecule in an amount effective to reduce or inhibit the yeast-to-filamentous growth transition, wherein the anti-fungal small molecule has the following chemical structure:

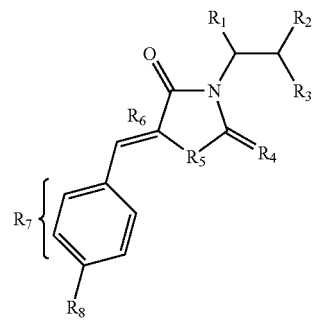

wherein $R_1$ is a carboxylic acid group or an ester group;

wherein $R_2$ is an alkyl group;

wherein $R_3$ is an alkyl group;

wherein $R_4$ is a sulfur atom or an oxygen atom;

wherein $R_5$ is a sulfur heteroatom or a nitrogen atom;

wherein $R_6$ is a double bond or a single bond;

wherein $R_7$ is an aromatic ring; and wherein $R_8$ is a halogen atom, a hydroxyl group, an alkyl group, an alkoxy group, or $N(CH_3)_2$.

In yet another alternate embodiment, the present invention is a method for controlling the yeast-to-filamentous growth transition in fungi comprising contacting a fungal cell with an anti-fungal small molecule in an amount effective to reduce or inhibit the yeast-to-filamentous growth transition, wherein the anti-fungal small molecule has the following chemical structure:

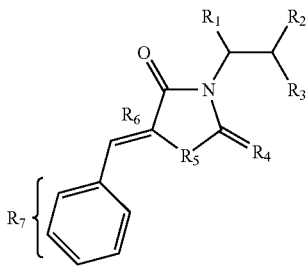

wherein $R_1$ is a carboxylic acid group or an ester group;
wherein $R_2$ is an alkyl group;
wherein $R_3$ is an alkyl group;
wherein $R_4$ is a sulfur atom or an oxygen atom;
wherein $R_5$ is a sulfur heteroatom or a nitrogen atom;
wherein $R_6$ is a double bond or a single bond; and
wherein $R_7$ is an aromatic ring.

In a preferred embodiment, the anti-fungal small molecule is an isomerically pure compound. In another preferred embodiment, the fungal cell is from the species *Candida albicans*. In yet another preferred embodiment, the fungal cell is from the genus consisting of *Candida*. In yet another preferred embodiment, the fungal cell is from the genera consisting of *Aspergillus, Blastomyces, Coccidioides, Histoplasma, Paracoccidioides,* and *Saccharomyces.*

The present invention is a method for treating fungal infections comprising contacting one or more fungal cells with an anti-fungal small molecule in an amount effective to control the fungal infection, wherein the anti-fungal small molecule is 5-(p-Bromobenzylidine)-α-isopropyl-4-oxo-2-thioxo-3-thiozolidineacetic acid.

In an alternate embodiment, the present invention is a method for treating fungal infections comprising contacting one or more fungal cells with an anti-fungal small molecule in an amount effective to control the fungal infection, wherein the anti-fungal small molecule is an analog of 5-(p-Bromobenzylidine)-α-isopropyl-4-oxo-2-thioxo-3-thiozolidineacetic acid.

In yet another alternate embodiment, the present invention is a method for treating fungal infections comprising contacting one or more fungal cells with an anti-fungal small molecule in an amount effective to control the fungal infection, wherein the anti-fungal small molecule has the following chemical structure:

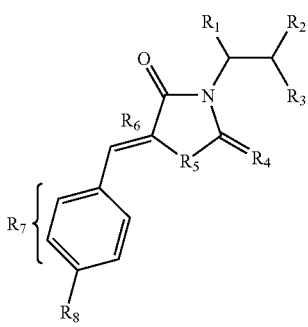

wherein $R_1$ is a carboxylic acid group or an ester group;
wherein $R_2$ is an alkyl group;
wherein $R_3$ is an alkyl group;
wherein $R_4$ is a sulfur atom or an oxygen atom;
wherein $R_5$ is a sulfur heteroatom or a nitrogen atom;
wherein $R_6$ is a double bond or a single bond;
wherein $R_7$ is an aromatic ring; and
wherein $R_8$ is a halogen atom, a hydroxyl group, an alkyl group, an alkoxy group, or $N(CH_3)_2$.

In yet another alternate embodiment, the present invention is a method for treating fungal infections comprising contacting one or more fungal cells with an anti-fungal small molecule in an amount effective to control the fungal infection, wherein the anti-fungal small molecule has the following chemical structure:

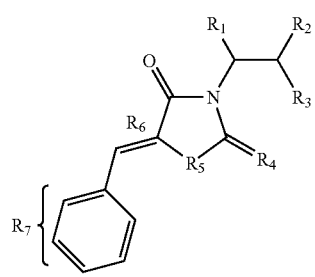

wherein $R_1$ is a carboxylic acid group or an ester group;
wherein $R_2$ is an alkyl group;
wherein $R_3$ is an alkyl group;
wherein $R_4$ is a sulfur atom or an oxygen atom;
wherein $R_5$ is a sulfur heteroatom or a nitrogen atom;
wherein $R_6$ is a double bond or a single bond; and
wherein $R_7$ is an aromatic ring.

In a preferred embodiment, the anti-fungal small molecule is an isometrically pure compound. In another preferred embodiment, the fungal cell is from the species *Candida albicans*. In yet another preferred embodiment, the fungal cell is from the genus consisting of *Candida*. In yet another preferred embodiment, the fungal cell is from the genera consisting of *Aspergillus, Blastomyces, Coccidioides, Histoplasma, Paracoccidloides,* and *Saccharomyces.*

DETAILED DESCRIPTION OF INVENTION

A. Overview

Figure 1:
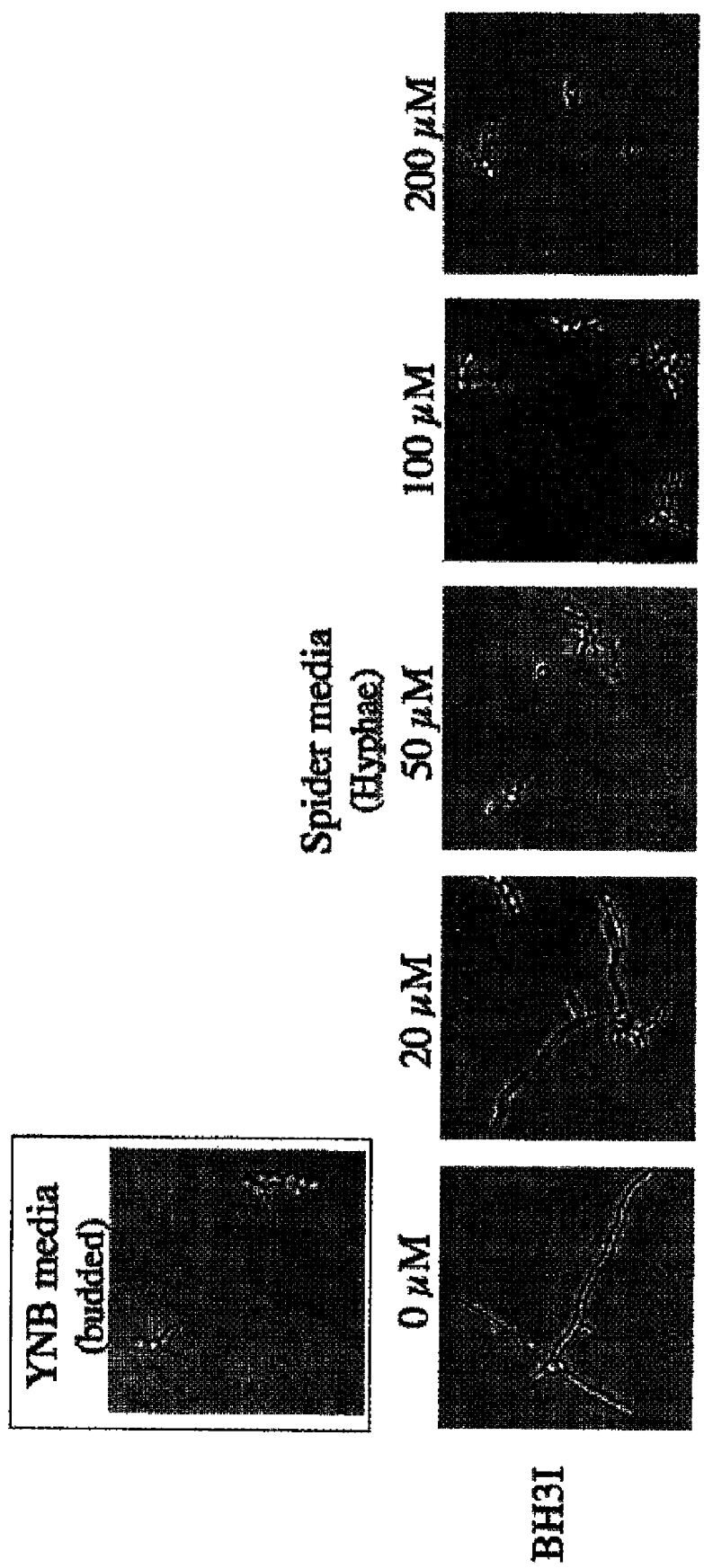
FIG. 1 shows Wild Type cells (SC3514) grown in YNB medium (0 µM BH3I-1) at 30° C. for 4 hours (upper panel) and Wild Type cells grown in Spider medium plus 0 µM, 20 µM, 50 µM, 100 µM and 200 µM BH3I-1 at 37° C. for 4 hours (lower panels). The number of cells inoculated is the same for each condition.

The present invention is based on the discovery of novel anti-fungal properties of a small molecule that was previously shown to induce programmed cell death in mammalian cells. The invention provides a method for treating or controlling fungal infections (such as those caused by C. albicans) through inhibition of the yeast-to-filamentous growth transition, which is important for the pathogenicity of C. albicans. The invention also provides a method for controlling the yeast-to-filamentous growth transition in in vitro systems.

The current generation of anti-fungal drugs works by inhibiting membrane biosynthesis and function and cell wall biosynthesis. BH3I-1 represents a potentially new class of anti-fungal drugs in that it inhibits a process (and presumably a molecular pathway) not targeted by the current anti-fungal therapies.

B. Anti-fungal Morphogenesis Properties of 5-(p-Bromobenzylidine)-α-isopropyl-4-oxo-2-thioxo-3-thiozolidineacetic acid (BH3I-1)

We have discovered that the small molecule BH3I-1 is effective for inhibiting fungal morphogenesis. As used herein, the terms "yeast-to-filamentous growth transition" and "fungal morphogenesis" refer to all yeast-to-hypha growth transitions and all yeast-to-pseudohypha growth transitions.

1. Assay for Inhibition of Fungal Morphogenesis.

A simple in vitro assay system was designed to detect inhibition of the yeast-to-filamentous growth transition in C. albicans [8]. In this assay, C. albicans cells are first grown under conditions that maintain them in a yeast growth form. The yeast-form cells are then transferred to the wells of an optical microplate containing (i) a medium that induces either the yeast-to-hypha transition (in wild type cells) or the yeast-to-pseudohypha transition (in a conditional pseudohyphal mutant strain) and (ii) varying concentrations of BH3I-1 (typically 0, 10, 30, 50, 100 and 200 μM BH3I-1). The plates are incubated for up to six hours at 37° C. (to test for the hyphal transition) or up to 24 hours 30° C. (to test for the pseudohyphal transition). The transition to filamentous growth (or lack thereof) is monitored in the optical microplates directly with a Nikon TE200 inverted microscope.

2. Strains and Media.

C. albicans SC3514 was used as the "wild type" strain to monitor the yeast-to-hypha transition. A "conditional pseudohyphal mutant" strain was used to monitor the yeast-to-pseudohypha transition [9]. The conditional strain harbors deletions of both native GRR1 alleles plus an introduced wild type copy of GRR1 under the control of the regulatable MET3 promoter [10]. Deletion of GRR1 was previously found to cause pseudohyphal growth [9].

Standard yeast growth media were used for these experiments. To maintain wild type cells in the yeast-form, cells were grown in YPD medium (1% Yeast Extract, 2% Peptone and 2% Dextrose) at 30° C. To induce hyphal growth in the wild type strain, cells were transferred to Spider medium (1% Nutrient broth, 1% mannitol, 2% $K_2HPO_4$) at 37° C. or to Lee's medium (0.5% $(NH_4)SO_4$, 0.02% $MgSO_4$, 0.5% NaCl, 1.25% glucose, supplemented with alanine, leucine, lysine, ornithine, phenylalanine threonine and biotin) at 37° C. To maintain the conditional pseudohyphal mutant strain in the yeast-form, cells were grown in YNB medium (Yeast Nitrogen Base, ammonium sulfate, succinic acid supplemented with the appropriate amino acids) at 30° C. This growth condition allows expression of the MET3p-driven GRR1 gene (and therefore yeast-form growth) [9]. To induce pseudohyphal growth, the conditional strain was transferred to YNB medium plus 2.5 mM methionine and 2.5 mM cysteine at 30° C. Methionine and cysteine in the growth medium represses the MET3p-driven GRR1 (gene and therefore induces pseudohyphal growth [9].

BH3I-1 was dissolved in dimethyl sulfoxide (DMSO) as a 5 mM stock and diluted into 100 μl of the appropriate medium at 10 μM, 50 μM, 100 μM and 200 μM final concentration. The control condition (no BH3I-1) included medium plus DMSO to a concentration equivalent to that of the BH3I-1-containing wells.

3. Bioinformatics.

BLAST searches of the NCBI, SOD, and CGD databases using the amino acid sequences of various BH3 domains has not identified any significant BH3 domains in Candida species. The closest match is from Candida glabrata with an expect (E) value score of 13. For comparison, an exact match from Homo sapiens generates an E value score of $1 \times 10^{-1}$. The lower the E value score, the more likely that the match contains a true homologue of the BH3 domain.

4. Results.

Wild type SC3514 C. albicans cells treated with BH3I-1 failed to undergo the yeast-to-hypha transition when transferred from YPD medium to either Spider medium or Lee's medium. The BH3I-1-treated SC3514 cells continued to divide as yeast cells in the hyphal-inducing media. The minimum inhibitory concentration (MIC) for the yeast-to-hypha transition was determined to be 50-100 μM BH3I-1 in both hyphal-inducing media. In contrast, greater than 90% of cells in the control condition (no BH3I-1) formed obvious hyphae in Spider (see FIG. 1, first panel in bottom row) and Lee's media (data not shown; results similar to FIG. 1).

Figure 2:
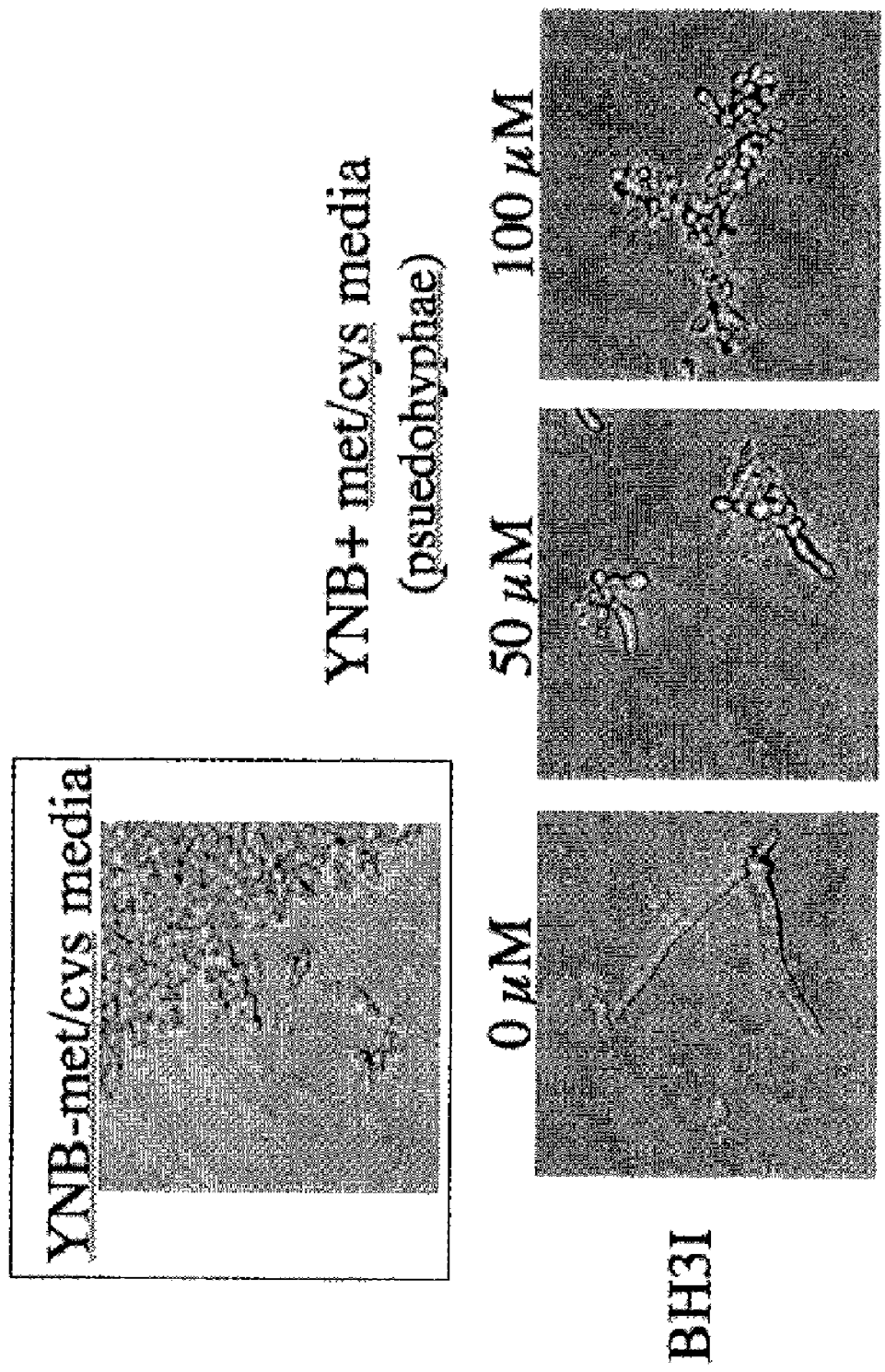
FIG. 2 shows conditional pseudohyphal mutant (grr1/grr1, MET3p-driven GRR1) cells grown in YNB medium (0 µM BH3I-1) at 30° C. for 24 hours (upper panel) and conditional pseudohyphal mutant cells grown in YNB+methionine/cysteine medium plus 0 µM, 50 µM and 100 µM BH3I-1 at 30° C. for 24 hours (lower panels). The number of cells inoculated is the same for each condition.

Conditional pseudohyphal mutant cells treated with BH3I-1 failed to undergo the yeast-to-pseudohypha transition when transferred from YNB medium to YNB plus methionine/cysteine medium. BH3I-1-treated conditional mutant cells continued to divide as yeast cells in the pseudohyphal-inducing medium (see FIG. 2). The MIC for the yeast-to-pseudohypha transition was determined to be 100 μM BH3I-1 in the pseudohyphal-inducing medium. Conditional mutant cells in the control condition (no BH3I-1) formed abundant pseudohyphae in the pseudohyphal-inducing medium (see FIG. 2, first panel in bottom row).

C. Structure and Analogs of 5-(p-Bromobenzylidine)-α-isopropyl-4-oxo-2-thioxo-3-thiozolidineacetic acid (BH3I-1)

Figure 3:
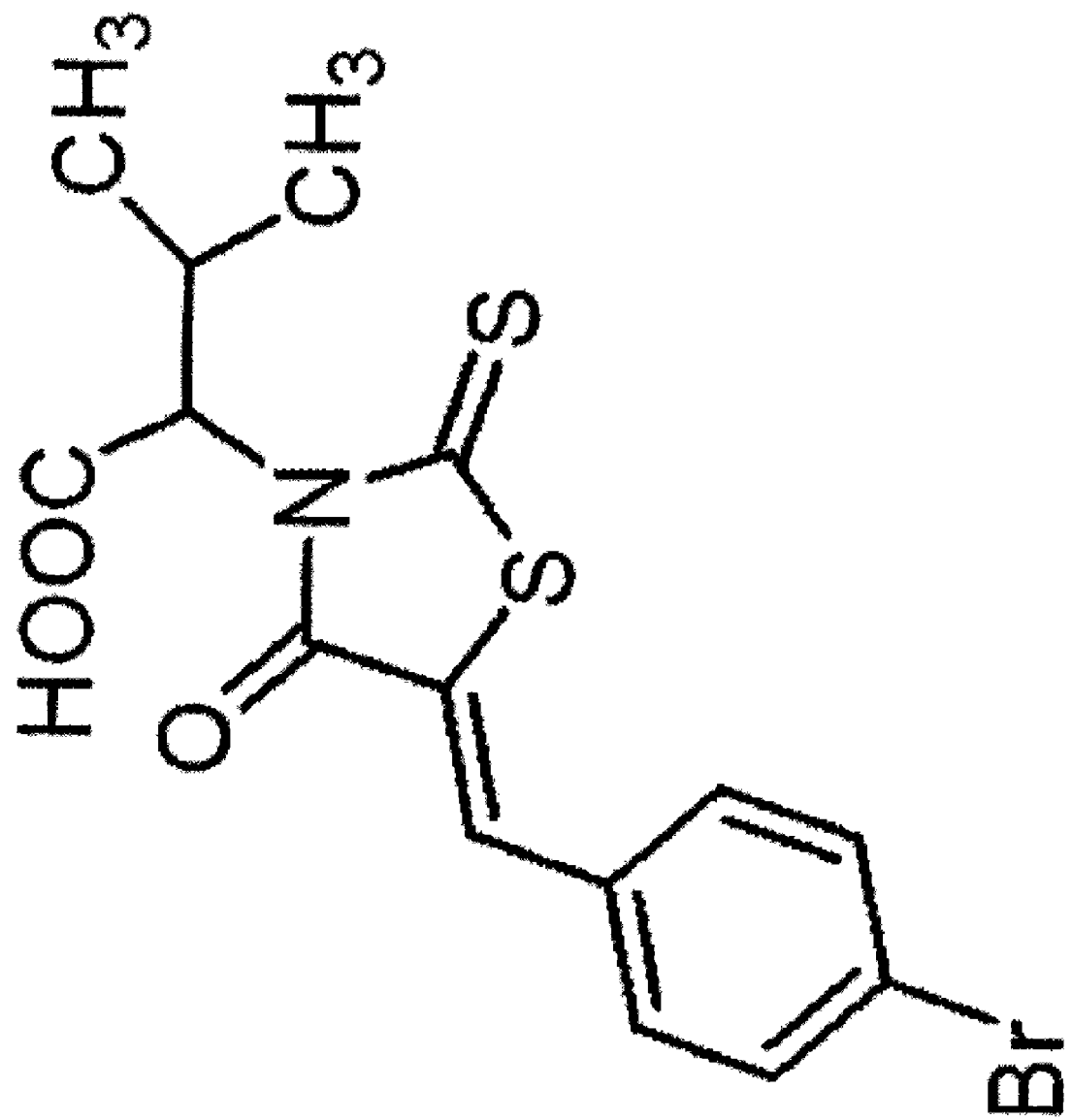
FIG. 3 is a schematic representation of the chemical structure of 5-(p-Bromobenzylidine)-α-isopropyl-4-oxo-2-thioxo-3-thiozolidineacetic acid (BH3I-1).

The anti-fungal morphogenesis small molecule BH3I-1 has the chemical structure shown in FIG. 3. This basic structure may be modified such that the resulting analogs of BH3I-1 also inhibit fungal morphogenesis.

Figure 4:
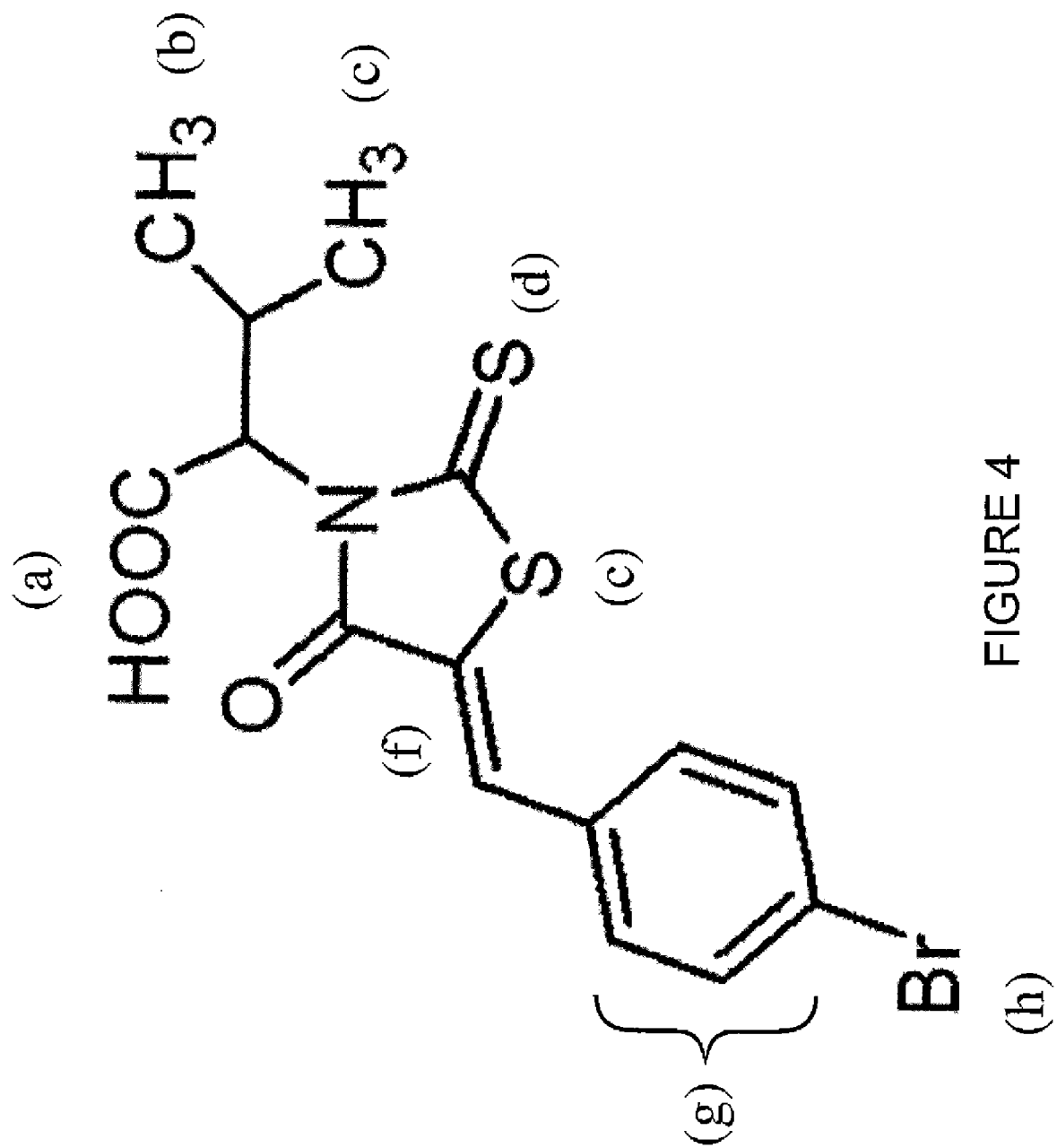
FIG. 4 is a schematic representation of the chemical structure of 5-(p-Bromobenzylidine)-α-isopropyl-4-oxo-2- thioxo-3-thiozolidineacetic acid (BH3I-1) with annotations to facilitate the discussion of analogs of BH3I-1 that inhibit fungal morphogenesis.

Referring to FIG. 4, in one embodiment of the present invention, analogs of BH3I-1 that inhibit fungal morphogenesis include, but are not limited to, modification the carboxylic acid group (a) to an ester group. The term "ester" is given its ordinary meaning as used in the field of organic chemistry. Esters include a carbonyl group bonded to an oxygen atom, where the oxygen atom is also bonded to an alkyl group.

In an alternate embodiment, analogs of BH3I-1 that inhibit fungal morphogenesis include, but are not limited to, replacement of the methyl group (b) with another alkyl group and/or replacement of the methyl group (c) with another alkyl group.

As used herein, the term "alkyl" is given its ordinary meaning as used in the field of organic chemistry. Alkyl or aliphatic groups typically contains any number of carbon atoms, for example, between one and 20 carbon atoms. In some embodiments, the alkyl group will contain at least one carbon atom. Typically, an alkyl group is a non-cyclic structure. In certain embodiments, the alkyl group is a methyl group or an ethyl group. The carbon atoms may be arranged in any configuration within the alkyl moiety, for example, as a straight chain (i.e., a n-alkyl such as methyl, ethyl, propyl, butyl, pentyl, hexyl, heptyl, octyl, nonyl, decyl, or undecyl) or a branched chain (e.g., a t-butyl group or an isoalkyl group such as isopropyl, isobutyl, isopentanyl, or isohexanyl). The alkyl moiety may contain none or any number of double or triple bonds within its structure, for example, as in an alkene, an alkyne, an alkadiene, an alkadiyne, an alkenyne, etc.

The alkyl group may contain any number of substituents. For example, the alkyl group may contain a halogen, an alkoxy (e.g., a methoxy, an ethoxy, a propoxy, an isopropoxy, a butoxy, or a pentoxy), an amine (e.g., a primary, secondary, or tertiary amine), or a hydroxide as a substituent. As one example, if the alkyl group is a methyl group, then the methyl group may be substituted to form, for instance, a halogenated methyl group such as chloromethyl, bromomethyl, or iodomethyl. In some embodiments of the invention, more than one substituent may be present. For example, the alkyl group may have two or more halogen atoms (for example, two chlorine atoms, or a chlorine and a bromine atom), or it may have a halogen and an alkoxy group.

As used herein the term "halogen," or equivalently, "halogen atom," is given its ordinary meaning as used in the field of chemistry. The halogens include fluorine, chlorine, bromine, iodine, and astatine. Preferably, the halogen atoms used in the present invention include one or more of fluorine, chlorine, bromine, or iodine. In certain embodiments of the invention, the halogen atoms found within the structure are fluorine, chlorine, and bromine; fluorine and chlorine; chlorine and bromine, or a single type of halogen atom.

As used herein the term "alkoxy" is given its ordinary meaning in the field of organic chemistry. An alkoxy group consists of an alkyl group covalently bound to an oxygen atom, where the oxygen atom is covalently bound to a carbon atom.

In some embodiments of the invention, the alkyl group may also contain one or more heteroatoms substituted within the alkyl group, such as a nitrogen atom (e.g., as in an amine such as a primary, secondary, or tertiary amine), an oxygen atom (as in an ether moiety) or a sulfur atom. In other embodiments of the invention, however, the main chain of the alkyl group is free of heteroatoms and includes carbon atoms.

As used herein, the term "heteroatoms" refers to atoms that can replace carbon atoms within an alkyl group without affecting the connectivity of the alkyl group; these typically include oxygen, nitrogen and sulfur atoms. Halogen atoms and hydrogen atoms are not considered to be heteroatoms; for example, a chlorine atom can replace a hydrogen atom within an alkyl group without affecting the connectivity of the alkyl group.

In one embodiment of the invention, analogs of BH3I-1 that inhibit fungal morphogenesis include, but are not limited to, replacement of the sulfur atom (d) with an oxygen atom.

In another embodiment of the invention, analogs of BH3I-1 that inhibit fungal morphogenesis include, but are not limited to, replacement of the sulfur heteroatom (e) with a nitrogen atom.

In yet another embodiment of the invention, analogs of BH3I-1 that inhibit fungal morphogenesis include reduction of the double bond (f) to a single bond.

In yet another embodiment of the invention, analogs of BH3I-1 that inhibit fungal morphogenesis include, but are not limited to, removal of the bromine atom (h), changing position of the bromine atom on the aromatic ring (g), inclusion of multiple bromine atoms at different positions on the aromatic ring (g), replacement of the bromine atom (h) with a different halogen atom, inclusion of non-bromine halogen atoms at different positions on the aromatic ring (g), replacement of the bromine atom (h) with a hydroxyl group, inclusion of hydroxyl groups at different positions on the aromatic ring (g), replacement of the bromine atom (h) with an alkyl group, inclusion of alkyl groups at different positions on the aromatic ring (g), replacement of the bromine atom (h) with an alkoxy group, inclusion of alkoxy groups at different positions on the aromatic ring (g), replacement of the bromine atom (h) with $N(CH_3)_2$, inclusion of $N(CH_3)_2$ at different positions on the aromatic ring (g), or any chemically possible combination of the foregoing.

As used herein, the term "aromatic ring" is given its ordinary meaning as used in the field of organic chemistry. An aromatic ring is a planar set of six carbon atoms that are connected by alternating single and double covalent bonds.

As used herein, the term "hydroxyl" is given its ordinary meaning as used in the field of organic chemistry. A hydroxyl group consists of an oxygen atom covalently bound to a hydrogen atom, where the oxygen atom is also covalently bound to a carbon atom.

According to some aspects of the invention, the BH3I-1 used in the methods for inhibiting fungal morphogenesis or in the methods for treating fungal infection may exist in different isomeric forms. BH3I-1 may be used in the methods of the invention as a substantially isomerically pure compound or as a mixture of isomers. As used herein the term "isomerically pure" means that one isomer will be present in an amount ranging from 51 to 100% relative to other isomers but not with respect to other impurities or other compounds that may be present. As used herein, the term "isomer" refers to an E or Z isomer, an R or S isomer, an enantiomer or a diastereomer.

D. Practical Applications

BH3I-1 is useful for a variety of in vitro and in vivo uses. In one application of the present invention, a fungal cell is contacted with BH3I-1 in an amount effective to reduce or inhibit fungal morphogenesis. It is intended that the fungal cell is contacted either in vitro or in situ, whereby in situ includes contacting a fungal cell in vivo or contacting a fungal cell on the surface of the skin. One of ordinary skill in the art would understand "contacting" to encompass putting a fungal cell into contact with BH3I-1, for example, in a culture plate or flask, whereby the fungal cell is placed into media containing BH3I-1. Further "contacting" would be understood by one of ordinary skill in the art to mean adding BH3I-1 to a fungal cell or population of fungal cells on the surface of the skin or parenterally or locally applying BH3I-1 to a subject such that the fungus in the subject is exposed to BH3I-1.

As used herein the term "fungal cell" is intended to encompass any cell originating from a fungal species or fungus. As used herein, the term "fungus" includes moulds, yeast and pathogenic yeast. A fungus includes, but is not limited to,

*Candida* (for example, *Candida albicans, Candida tropicalis, Candida dubliniensis, Candida parapsilosis, Candida keyfyr, Candida guilliermondii, Candida inconspicua, Candida famata, Candida krusei,* and *Candida lusitaniae*), *Aspergillus* (for example, *Aspergillus nidulans* and *Aspergillus fumigatus*), *Saccharomyces* (for example, *Saccharomyces cerevisiae*), *Blastomyces* (for example, *Blastomyces dermatitidis*), *Coccidioides* (for example, *Coccidioides immitis*), *Histoplasma* (for example, *Histoplasma capsulatum*), and *Paracoccidioides* (for example, *Paracoccidioides brasiliensis*).

As used herein, the terms "treating" and "treat" are intended to include preventing, ameliorating, curing, or reducing symptoms of fungal infections. As used herein, the term "subject" is any animal in need of treatment, including humans, primates and other mammals such as equines, cattle, swine, sheep, goats, primates, mice, rats, and pets in general, including, but not limited to, dogs, cats, guinea pigs, ferrets, and rabbits.

The present invention can be used to treat fungal infections in subjects deemed medically of either having a fungal infection or being at significant risk of developing a fungal infection. A subject at risk of developing a fungal infection is a subject that has been exposed to a fungus or is susceptible to exposure to a fungus. For instance, subjects that are susceptible to exposure to a fungus includes those subjects who work in, live in or travel to areas with high fungal content or infectivity rates, as well as those subjects having particular susceptibility to fungal infection as a result of medical conditions or therapies. Examples of subjects having particular susceptibility to fungal infections arising from medical conditions or therapies include, but are not limited to, an immunocompromised subject (the compromised state of the subject's immune system could be the result of an infectious disease such as AIDS, an inherited disorder, or a treatment protocol for, but not limited to, cancer, organ transplants, or infectious diseases) or a subject having a central venous catheter.

Although the invention has been described in connection with specific embodiments and applications thereof the invention is capable of further modifications and/or applications, and this application is intended to cover any and all variations, uses, or adaptations of the invention that fall within the scope of the invention as described herein. The appended claims are therefore intended to cover all such variations, uses and adaptations as fall within the true spirit and scope of the invention.

REFERENCES

1. Edmond, M. B., S. E. Wallace, D. K. McClish, M. A. Pfaller, R. N. Jones and R. P. Wenzel (1999). Nosocomial bloodstream infections in United States hospitals: a three-year analysis. Clin. Infect. Dis., 29:239-244.
2. Schmidt-Westhausen, A., R. A. Schiller, H. D. Pohle, P. A. Reichart (1991). Oral *Candida* and Enterobacteriaceae in HIV-1 infections correlation with clinical candidiasis and antimycotic therapy. J. Oral Pathol. Med., 20: 467-72.
3. Warnock, D. W. (2007). Trends in the epidemiology of invasive fungal infections. Jpn. J. Med. Mycol., 48:1-12.
4. Sudbery, P., N. Gow and J. Berman (2004). The distinct morphogenic states of *Candida albicans*. Trends Microbiol. 12:317-24.
5. Lo, H. J., J. R. Kohler, B. DiDomenico, D. Loebenberg, A. Cacciapuoti, and G. R. Fink (1997). Nonfilamentous *C. albicans* mutants are avirulent. Cell 90:939-49.
6. Madeo, F., E. Herker, C. Maldener, S. Wissing, S. Lachelt, M. Herlan, M. Fehr, K. Lauber, S. J. Sigrist, S. Wesselborg and K. Frohlich (2002). A caspase-related protease regulates apoptosis in yeast. Mol. Cell. 9:911-17.
7. Fedorova, N. D., J. H. Badger, G. D. Robson, J. R. Wortman and W. C. Nierman (2005). Comparative analysis of programmed cell death pathways in filamentous fungi. BMC Genomics 6:177-191.
8. Toenjes, K. A., S. M. Munsee, A. S. Ibrahim, R. Jefferey, J. E. Edwards and D. I. Johnson (2005). Small-molecule inhibitors of the budded-to-hyphal-form transition in the pathogenic yeast *Candida albicans*. Antimicrob. Agents Chemother. 3:963-72.
9. Butler, D. K., O. All, J. Goffena, T. Loveless, and K. A. Toenjes (2006). The GRR1 gene of *Candida albicans* is involved in the negative control pseudohyphal morphogenesis. Fungal Genetics and Biology. 43: 573-582.
10. Care, R. S., K. M. Trevethick, K. M. Binley, and P. E. Sudbery (1999). The MET3 promoter: a new tool for *Candida albicans* molecular genetics. Mol. Microbiol. 34: 792-798.
11. Saville, S. P., A. L. Lazzell, C. Monteagudo and J. L. Lopez-Ribot (2003). Engineered control of cell morphology in vivo reveals distinct roles for yeast and filamentous forms of *Candida albicans* during infection. Eukaryotic Cell 2:1053-60.

We claim:

1. A method for controlling yeast-to-filamentous growth transition in fungi comprising contacting a fungal cell with an anti-fungal small molecule in an amount effective to reduce or inhibit the yeast-to-filamentous growth transition, wherein the anti-fungal small molecule is 5-(p-Bromobenzylidine)-α-isopropyl-4-oxo-2-thioxo-3-thiozolidineacetic acid, and wherein the species of the fungal cell is selected from the group consisting of *Candida albicans, Candida dubliniensis, Candida tropicalis, Candida parapsilosis* and *Candida rugosa*.

2. A method for treating fungal infections comprising contacting one or more fungal cells with an anti-fungal small molecule in an amount effective to control the fungal infection, wherein the anti-fungal small molecule is 5-(p-Bromobenzylidine)-α-isopropyl-4-oxo-2-thioxo-3-thiozolidineacetic acid, and wherein the species of the fungal cell is selected from the group consisting of *Candida albicans, Candida dubliniensis, Candida tropicalis, Candida parapsilosis* and *Candida rugosa*.

* * * * *